United States Patent [19]
Arsenault et al.

[11] Patent Number: 6,113,008
[45] Date of Patent: Sep. 5, 2000

[54] ACTUATOR SYSTEM FOR SPRAYING A FORMULATION ONTO A HOST

[75] Inventors: Cathleen M. Arsenault, Fridley; James A. Wilson, North St. Paul; David J. Wirtanen, Stillwater, all of Minn.

[73] Assignee: 3M Innovative Properties Company, St. Paul, Minn.

[21] Appl. No.: 09/137,378

[22] Filed: Aug. 20, 1998

[51] Int. Cl.[7] .................................................. B05B 7/32
[52] U.S. Cl. ...................... 239/337; 239/288; 222/402.13
[58] Field of Search ................... 239/288, 288.3, 239/288.5, 274, 337; 222/162, 402.2, 402.13; 128/200.23, 200.18, 200.14, 200.22; 604/289, 290, 310

[56] References Cited

U.S. PATENT DOCUMENTS

| | | | |
|---|---|---|---|
| 3,275,000 | 9/1966 | Bowen | 239/337 |
| 3,306,252 | 2/1967 | Knight et al. | 239/337 |
| 3,357,427 | 12/1967 | Wittke et al. | 222/402.2 |
| 3,549,055 | 12/1970 | Gatland | 222/402.13 |
| 3,744,678 | 7/1973 | Beres et al. | 222/402.13 |
| 3,913,842 | 10/1975 | Singer . | |
| 3,936,000 | 2/1976 | Weyn | 222/402.13 |
| 4,087,022 | 5/1978 | Zanetti-Streccia . | |
| 4,158,361 | 6/1979 | Kotuby | 222/402.13 |
| 4,226,340 | 10/1980 | Troesch et al. . | |
| 4,355,740 | 10/1982 | Wolf . | |
| 4,407,481 | 10/1983 | Bolton et al. . | |
| 4,420,099 | 12/1983 | Pizzurro et al. . | |
| 4,819,834 | 4/1989 | Thiel . | |
| 5,088,849 | 2/1992 | Johnson et al. | 604/310 |
| 5,122,056 | 6/1992 | Barbee | 128/200.23 |
| 5,290,539 | 3/1994 | Marecki . | |

FOREIGN PATENT DOCUMENTS 1386695  12/1975  United Kingdom .

*Primary Examiner*—Andres Kashnikow
*Assistant Examiner*—Dinh Q. Nguyen
*Attorney, Agent, or Firm*—MarySusan Howard; Ted K. Ringsred; Robert W. Sprague

[57] ABSTRACT

Actuator system is used to dispense a defined volume of a formulation from a pressurized vial. The system houses the vial in a receptacle of a base section that also includes a dispensing section (e.g., a funnel) through which the formulation is sprayed. The system includes a sleeve that fits over at least the vial and that can be pumped by the user to controllably spray the formulation from the vial onto the host animal. For instance, in a preferred mode of operation, the user places the system onto the host at the desired treatment site and then pushes or pulls down on the sleeve. This actuates a valve mechanism on the vial to spray an amount of the formulation through the dispensing section onto the host.

17 Claims, 8 Drawing Sheets

ACTUATOR SYSTEM FOR SPRAYING A FORMULATION ONTO A HOST

FIELD OF THE INVENTION

This invention is in the field of devices that deliver therapeutically effective liquids onto a host, such as a human. More specifically, this invention relates to an actuator system for spraying therapeutically effective liquids from a vial onto a host with great precision, accuracy and control.

BACKGROUND OF THE INVENTION

Transtissue drug delivery is a non-invasive therapeutic method in which a drug is first placed onto a tissue of a host animal and then caused to penetrate into the tissue in furtherance of the desired therapeutic treatment. Transtissue drug delivery can be used to treat topical, local, or systemic medical conditions. Delivery can occur across a number of different tissues including the skin, mucosal membranes, or the like. Delivery through the skin is generally referred to as "transdermal" drug delivery.

Transdermal drug delivery is typically accomplished by using a covering element in the form of a transdermal patch device that is attached to the host at the desired drug delivery site. A conventional "peel and place" transdermal patch device generally includes a drug-in-adhesive layer sandwiched between an impermeable backing and a release liner. At the time of use, the release liner is easily removed so that the patch can be attached to the host, adhesive side down. The impermeable backing thus traps the drug between the backing and the attachment site of the host. Over time, the drug penetrates into the host, or is topically active, in furtherance of the desired therapeutic treatment. Optionally, the drug-in-adhesive formulation may include one or more compounds known as penetration enhancers that increase the permeability of the tissue to the drug.

Although the peel and place type of transtissue drug delivery device has been an extremely effective means to accomplish drug delivery for a wide variety of medical conditions, there are still a number of ways in which transtissue drug delivery could be improved. For instance, the structure of the conventional peel and place patch currently involves a manufacturing operation requiring the drug-in-adhesive to be coated onto a substrate, such as the release liner or the impermeable backing as the case may be. This kind of coating step involves substantial expense in terms of capital equipment, utilities, manufacturing space, and human resources needed to carry out the coating operation. To avoid such expense, it would be desirable if a way could be found to eliminate the need for such a coating step.

As another example, the use of a release liner is less than environmentally friendly in the sense that the release liner becomes an item of waste that must be discarded in some fashion after being removed from its patch. It would be desirable if a way could be found to avoid this kind of waste.

Another area of improvement concerns the ability to more effectively control the rate of drug delivery. For current patches, the rate of drug delivery is initially relatively high when the concentration of the drug in the patch is still relatively high. However, as the drug is depleted, the rate of drug delivery slows down. It would be desirable to provide a patch that is characterized by a steady, consistent rate of drug delivery over a longer period of time.

Assignee's co-pending U.S. patent application entitled SPRAY ON BANDAGE AND DRUG DELIVERY SYSTEM having docket number 53867USA5A and filed Aug. 20, 1998 (incorporated herein by reference in its entirety), describes a novel "patch in a bottle" technology in which a fluid composition, e.g. an aerosol spray, is applied onto a substrate as a fluid, but then dries to form a composite covering element, such as a patch, having a tack free outer surface covering an underlying adhesive that helps adhere the patch to the substrate. The fluid compositions have a unique chemical formulation that allows such composite patches to form in situ. Specifically, the fluid compositions include a tacky component, such as an adhesive, and a film forming, non-tacky component. The non-tacky and tacky components are selected to be immiscible with each other so that the components undergo phase separation as the fluid composition dries. The non-tacky component has characteristics that cause it to seek the surface of a coating, where it dries to form a non-tacky protective film. The tacky component dries below this film, providing the bottom surface of the patch with a sufficient tack to adhere to the substrate. One or more pharmacologically active agents are easily incorporated into the fluid compositions so that the fluid compositions and corresponding patches can be used for transtissue drug delivery, e.g. transdermal drug delivery, delivery through a mucosal membrane, or the like.

When applying the patch in bottle formulations to a host in which such formulations include a pharmacologically active agent, it is important that the application of the formulations be accurately controlled so that the patient receives a proper dosage. What is needed is a way to administer these formulations in a manner that allows such control.

SUMMARY OF THE INVENTION

The present invention provides a method and system that accurately and precisely administers formulations from a vial onto any desired surface. The invention is particularly suitable for controllably and consistently dispensing uniform dosages of therapeutically effective compositions, such as the "patch in a bottle" formulations of Assignee's co-pending application, onto a host animal, such as a human or other mammal.

As an overview, the system preferably is used to dispense a defined volume of a formulation from a pressurized vial. The system houses the vial in a receptacle of a base section that also includes a dispensing section (e.g., a funnel) through which the formulation is sprayed. Advantageously, when used with therapeutically active, sprayable compositions, such as the patch in a bottle formulations of Assignee's copending application, the dispensing section can be sized and shaped so that a precisely sized patch formed from a precise volume of a precise composition is formed on the host. This helps to ensure that the resultant patch very accurately delivers the desired dosage of a pharmacologically active agent to the host.

The system preferably includes a sleeve that fits over at least the vial and that can be pumped by the user to controllably spray the formulation from the vial onto the host animal. For instance, in a preferred mode of operation, the user places the system onto the host at the desired treatment site and then pushes or pulls down on the sleeve. This actuates a valve mechanism on the vial to spray an amount of the formulation through the dispensing section onto the host. The spray travels through the dispensing section along a pathway having a substantially linear longitudinal axis so that as much of the spray as possible reaches the host. Preferably, the formulation can travel from the vial to the host over a relatively short distance. This also minimizes the amount of formulation that would be lost during spraying.

As another advantage, the use of such a linear dispensing section allows a precise amount of uniformly sized droplets of the formulation to be sprayed from a uniform height (determined by the height of the dispensing section) over a uniform area (determined by the outlet of the dispensing section). As a consequence, a uniform dosage of the formulation is applied to the host each time that the system is actuated, because, with each actuation, the dosage will cover substantially the same surface area at substantially the same thickness.

The sleeve itself also offers many performance advantages. First, the sleeve helps to maintain proper alignment between the vial and the base section. Second, the sleeve forms a protective envelope around the vial. The sleeve keeps the vial from falling out of the base section and protects the vial during storage, shipping, or use. Third, the sleeve makes it easier for the user to dispense an amount of formulation from the vial, especially for the elderly.

In one aspect, the present invention provides an actuator system for applying a sprayable formulation from a vial onto a limited surface area of a host. The system includes a base section comprising a dispensing section having an interior through which an amount of the formulation can be sprayed onto the surface area. The dispensing section comprises a throat at which the amount of the formulation enters the dispensing section and a mouth at which the amount of the formulation exits the dispensing section. The base section also includes a receptacle comprising a structure that operationally couples the vial to the dispensing section so that the formulation can be dispensed from the vial into the throat of the dispensing section. A sleeve is adapted to fit over at least a portion of the vial when the vial is positioned in the receptacle. The sleeve has a range of motion extending from a first position to a second position, wherein movement of the sleeve from the first position to the second position causes said amount of formulation to be dispensed into the dispensing section. The vial is closed when the sleeve is in the first position, and the sleeve is biased toward the first position.

In another aspect, the present invention relates to an actuator system for applying a sprayable formulation from a vial onto a limited surface area of a host. The system includes a base section that includes a dispensing section through which an amount of the formulation can be sprayed onto said surface area. The dispensing section comprises a throat at which the amount of the formulation enters the dispensing section and a mouth at which the amount of the formulation exits the dispensing section. The dispensing section comprises at least one vent in open communication with the ambient. The base section also includes a receptacle comprising a structure that operationally couples the vial to the dispensing section so that the formulation can be dispensed from the vial into the throat of the dispensing section.

In another aspect, the present invention relates to an actuator system for applying a sprayable formulation from a vial onto a defined surface area of a host. The actuator system comprises a base section comprising a dispensing section. The dispensing section includes a pathway through which an amount of the formulation may be sprayed from a uniform height over said surface area. The dispensing section comprises a substantially linear longitudinal axis extending from a throat at which the amount of formulation enters the dispensing section to a mouth at which the formulations exits from the dispensing section. A receptacle comprises a structure that operationally couples the vial to the dispensing section so that the amount of the formulation can be dispensed from the vial through the dispensing section. The receptacle comprises a cup for housing at least a portion of the vial. The cup comprises one or more vents providing open communication between the cup and the ambient.

BRIEF DESCRIPTION OF THE DRAWINGS

The above mentioned and other advantages of the present invention, and the manner of attaining them, will become more apparent and the invention itself will be better understood by reference to the following description of the embodiments of the invention taken in conjunction with the accompanying drawings, wherein.

DETAILED DESCRIPTION OF THE PRESENTLY PREFERRED EMBODIMENTS

Figure 1:
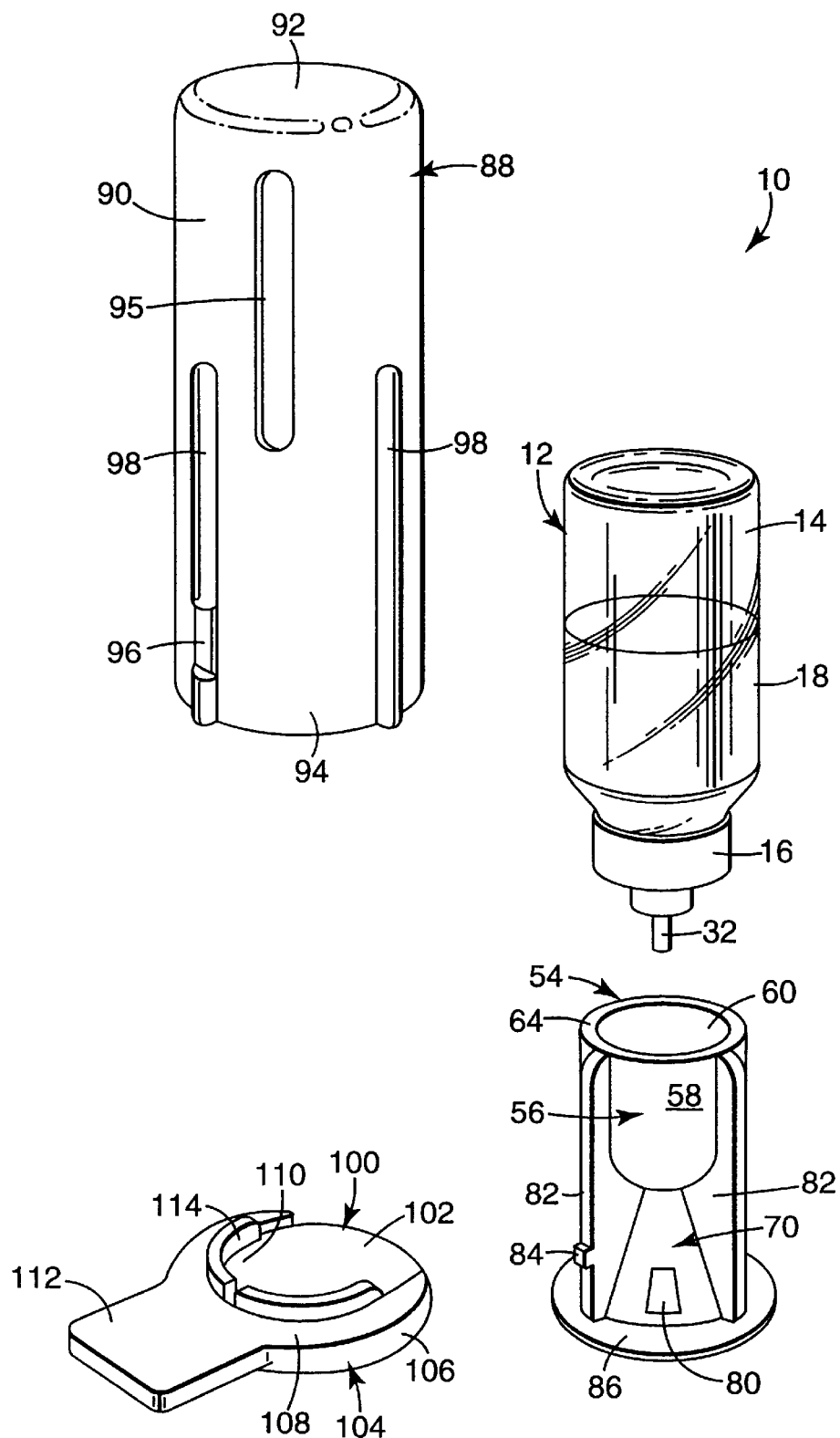
FIG. 1 is an exploded perspective view of an actuator system of the present invention.
Figure 2:
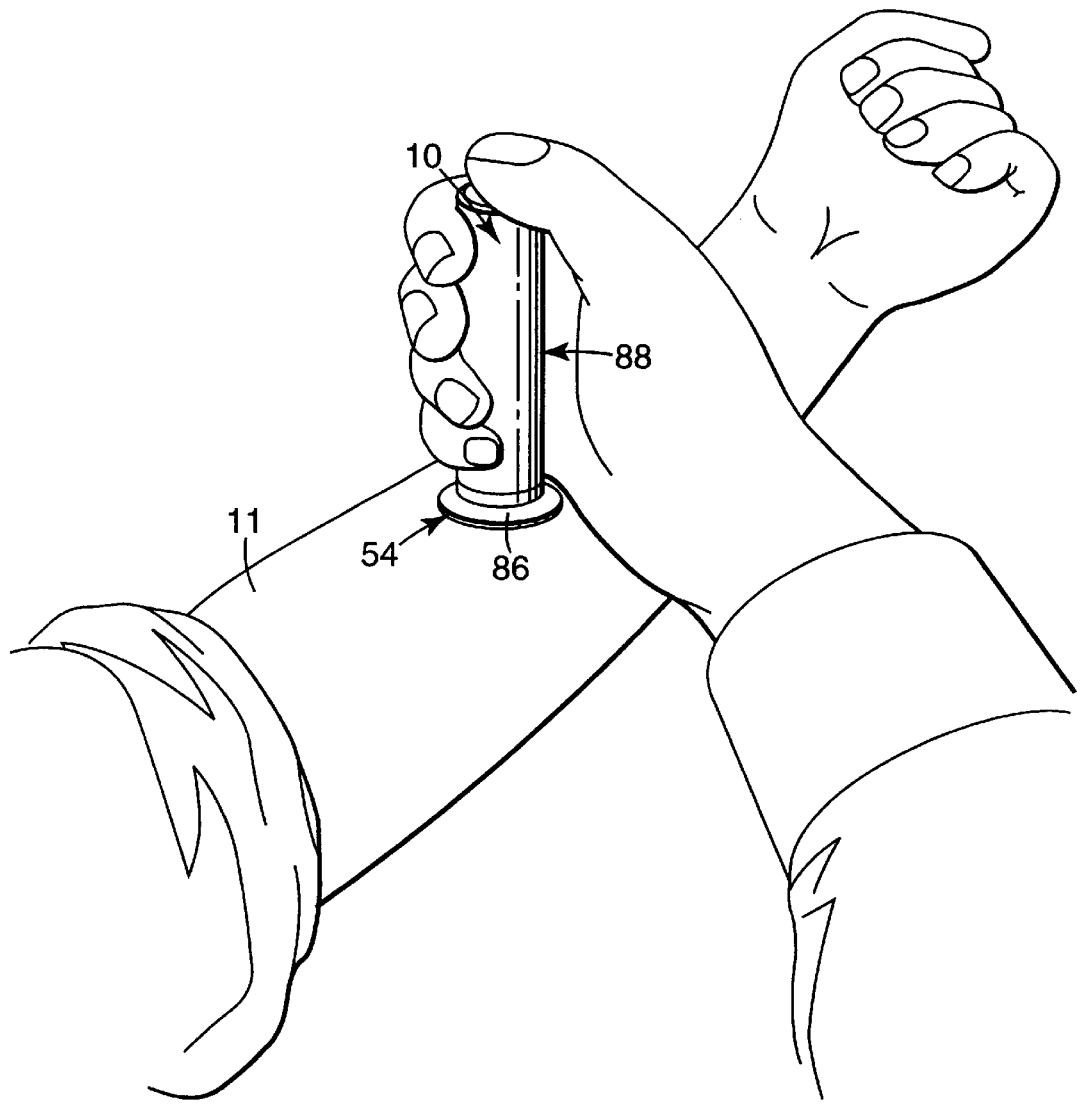
FIG. 2 shows the actuator system of FIG. 1 being used on a host.
Figure 3A:
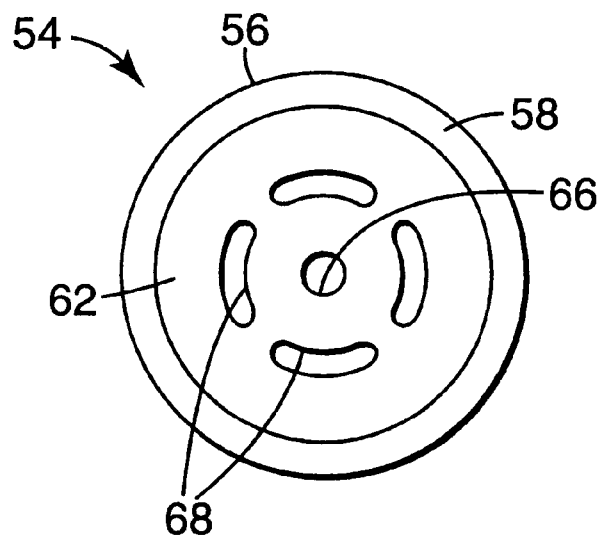
FIG. 3a is a top view of the base section used in the actuator system of FIG. 1, showing the centrally located orifice and vent holes located around that orifice in the bottom of the receptacle portion of the base section.
Figure 3B:
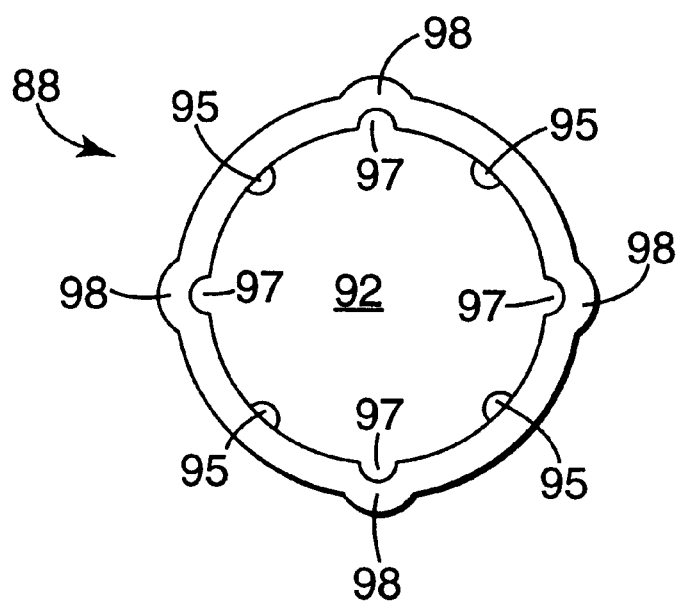
FIG. 3b is an end view of the sleeve from the actuator system of FIG. 1, when the inside of the sleeve is shown.

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

FIGS. 1 through 4a show a preferred embodiment of an actuator system 10 of the present invention that may be used to spray precise amounts of a sprayable formulation, such as a transdermal drug delivery formulation, over a precise surface area of a host animal 11, preferably a mammal, more preferably a human. Actuator system 10 is particularly suitable for dispensing the "patch in a bottle" compositions of Assignee's co-pending U.S. patent application titled SPRAY ON BANDAGE AND DRUG DELIVERY SYS- TEM having Docket No. 53867USA5A and filed Aug. 20, 1998, the entirety of which is incorporated herein by reference.

Actuator system houses vial 12 and is used to dispense a precise amount of supply 18 onto host 11. Vial 12 includes canister body 14 sealed at one end by a cover in the form of valved dispensing element 16. Supply 18 of the formulation to be sprayed is stored inside canister body 14. Canister body 14 can be formed from a wide variety of materials, but desirably is formed from one or more materials that are chemically inert with respect to supply 18 and are suitable for use in connection with medically active compositions. Representative examples of suitable materials include a polymer such as polyester, polycarbonate, acrylic polymer, polyolefin, polyurethane, silicone, silicone-polyurea, silicon polyurethane, fluoropolymer, epoxy, combinations of these or the like; glass; glass coated with on or more polymers listed above; stainless steel; aluminum; polymer coated (e.g., an epoxy coating) aluminum; combinations of these and the like. Vials made from transparent or translucent materials, such as glass, are preferred, because such materials allow the amount and integrity of supply 18 stored in canister body 14 to be visually inspected. Particularly preferred aluminum vials are commercially available from Minnesota Mining and Manufacturing Company (3M), St. Paul, Minn., and come in a variety of sizes ranging from 5 $cm^3$ to 22.5 $cm^3$. Particularly preferred polymer coated glass vials are commercially available from Wheaton Science Products, a division of Lawson Mardon Wheaton, member of the Alusuisse-Lonza Group and come in a variety of sizes ranging from 10 ml to about 120 ml.

Valved dispensing element 16 may be of any structure that allows an amount of supply 18 to be dispensed on demand onto host 11. For example, valved dispensing element 16 may be in the form of an element that is biased towards a closed position in the absence of an actuating force acting against at least a portion of element 16, but is opened to dispense an amount of the formulation in the presence of such an actuating force. In such a form, valved dispensing element 16 may be of the continuous type through which the formulation is continuously sprayed when valved dispensing element 16 is opened. As another option, and more preferably, valved dispensing element 16 may be of the metered dose type which dispenses a precise amount of the formulation each time that the valve is actuated. The metered dose type of valve is particularly beneficial in applications in which an accurate dose of a pharmacologically active agent is to be delivered to host 11.

Continuous and metered dose valve elements are well known in the art and have been described in U.S. Pat. Nos. 5,290,539 (Marecki); 4,819,834 (Thiel); 4,407,481 (Bolton); 3,052,382 (Gawthrop); 3,049,269 (Gawthrop); 2,980,301 (DeGorter); 2,968,427 (Meshberg); 2,892,576 (Ward); 2,721,010 (Meshberg), all of which are incorporated herein by reference in their respective entireties. Continuous and metered dose valve elements are also commercially available from 3M. Metered dose valve elements are available from 3M that dispense precise amounts of formulation with each actuation in discrete volumes in the range from 25 microliters to 100 microliters.

Figures 5A, 5B:
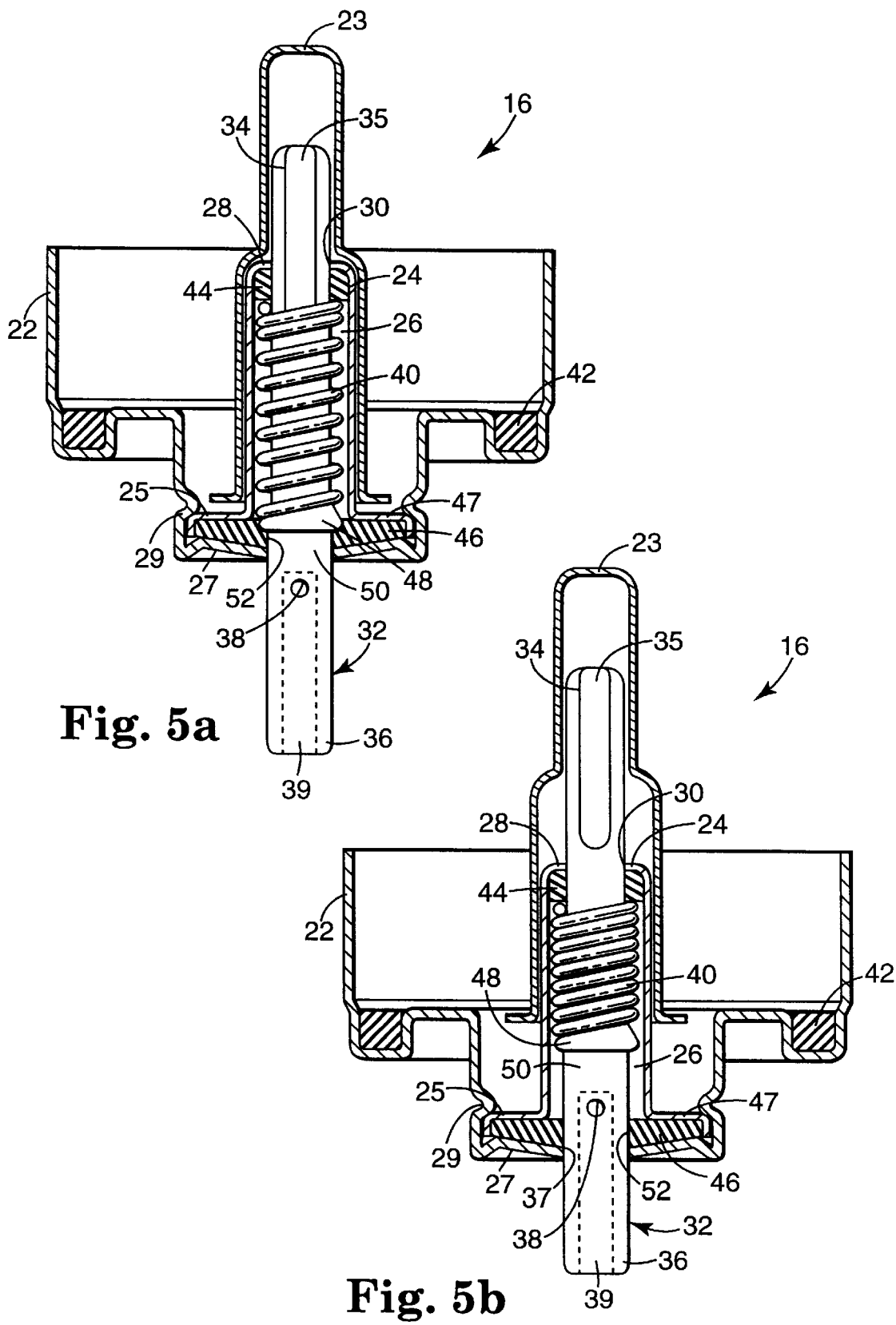
FIG. 5a is a cross-sectional side view of a preferred metered dose, valved dispensing element suitable for use in the acuator system of FIG. 1, wherein the valved dispensing element is shown in a closed position with the stem extended.
FIG. 5b is a cross-sectional side view of the valved dispensing element of FIG. 5a, wherein the valved dispensing element is in an open position with the stem being depressed.

A cross-section of a representative valved dispensing element 16 configured for metered dose delivery of supply 18 is shown in FIGS. 5a and 5b. Element 16 includes mounting cup 22 that sealingly fits in a conventional fashion over the open end of canister body 14 (not shown in FIGS. 5a and 5b). Metering tank 24 defines metering chamber 26 and is secured inside mounting cup 22 by lip 25 that engages rim 29. Bottom 28 of metering tank 24 fits inside optional retaining cup 23. Retaining cup 23 is in open communication with the inside of canister body 14 so that retaining cup 23 is easily filled with aliquots of supply 18.

Stem 32 extends through and beyond both ends of metering tank 24. One end 34 of stem 32 extends though orifice 30 of tank bottom 28 and into the interior of retaining cup 23. The other end 36 of stem 32 passes out of metering tank 24 and through orifice 37 of mounting cup in order to extend above element 16. Proximal to stem end 34, stem 32 includes inlet channel 35 that allows formulation inside retaining cup 23 to enter metering chamber 26 when stem 32 is in the closed, extended position of FIG. 5a. Access through inlet channel 35 is blocked as stem 32 is depressed from the closed position of FIG. 5a to the open position of FIG. 5b. Proximal to stem end 36, outlet channel 39 allows formulation inside metering chamber 26 to escape (i.e., be dispensed) into the ambient. Access from metering chamber 26 to outlet channel 39 occurs through orifice 38 when stem 32 is in the open, depressed position of FIG. 5b. Access through orifice 38 is blocked, and hence no formulation in metering chamber 26 can be dispensed, when stem 32 is in the extended, closed position of FIG. 5a. Spring 40 biases stem 32 toward the extended, closed position of FIG. 5a.

Ferrule gasket 42 helps to establish a liquid tight seal between mounting cup 22 and canister body 14. Tank seal gasket 44 helps to establish a liquid tight seal between stem 32 and metering tank 24 as stem 32 passes through orifice 30 into retaining cup 23. Diaphragm 46 helps to establish a liquid tight seal at the open end 47 of metering tank 24 and around end 36 of stem 32. Shoulder 48 of stem 32 bears against diaphragm 46 as narrow neck portion 50 of stem 32 passes through diaphragm orifice 52.

Valved dispensing element 16 is biased to the closed position of FIG. 5a in which stem 32 is fully extended with shoulder 48 seated against diaphragm 46. In this position, inlet channel 35 fluidly connects the inside of retaining cup 23 with metering chamber 26. This allows a metered amount of formulation to enter metering chamber 26 from retaining cup 23. In the meantime, access into outlet channel 39 via orifice 38 is blocked, so that the metered amount of formulation cannot escape from metering chamber 26.

To dispense the metered amount of formulation from metering chamber 26, valve stem 32 is depressed to the position of FIG. 5b. As valve stem 32 is moved to this position, access to inlet channel 35 becomes blocked, thus isolating the metered amount of formulation inside of metering chamber 26. Further depression of valve 32 causes orifice 38 to move into metering chamber 26, opening access to outlet channel 39. As a consequence, the metered amount of formulation inside metering chamber 26 becomes exposed to the ambient. Rapid volatilization of the propellant included in the formulation occurs and causes the metered dose to be dispensed from valve stem 32. When the force acting to depress valve stem 32 is released, spring 40 biases stem 32 back to the position of FIG. 5a, where metering tank 24 is filled with a metered amount of formulation that is ready to be dispensed again, on command, so long as enough supply 18 remains inside canister body 14.

One important consideration when using a metered dose valve such as element 16 shown in FIGS. 5a and 5b concerns the material that is used to form gaskets 42, 44, and/or 46. The material of each gasket is preferably an elastomer that undergoes very little if any weight loss (due to extraction into the particular formulation constituting supply 18), swelling, or leaking when exposed to supply 18 for extended periods of time. The elastomer should also be inert with respect to the formulation so that the properties of supply 18 and/or the material do not undergo chemical or physical changes that might affect the desired kind and degree of performance of actuator system 10 or supply 18.

In choosing a suitable elastomer, or elastomers, preferred elastomers show less than 3% weight loss, preferably less than 1% weight loss, when exposed to a sample of the formulation to be stored in canister body 14 as supply 18. To test a gasket for weight loss, the gasket is initially weighed and then placed into the sample for 96 hours at 25° C. After such extraction period is carried out, the gasket is dried and weighed again. The percent weight loss can then be easily calculated as (1−r)×100%, where r is the ratio of the after-extraction weight to the before-extraction weight.

Desirable elastomers provide gaskets having inner and outer diameters that each independently show less than about 5%, preferably less than about 2%, swelling or shrinkage (as the case may be) when exposed to any component, or combination of components to be incorporated into the formulation to be stored in canister body 14 as supply 18. To test for dimensional changes resulting from exposure to a particular chemical (e.g., a solvent, propellant, penetration enhancer, or combinations thereof), a minimum of four samples of the gasket material to be tested are placed inside a swelling cell that may be sealed from the ambient. This is particularly important when the chemical to be tested is a volatile component such as a propellant. The materials should be secured to prevent movement around the cell. Stapling the samples to polyethylene is suitable for this. Each sample may be assigned a number or the like for easy identification. The inner and outer diameters of each sample are measured to within 0.0005 inches (0.0013 cm). The measurements are recorded. Then, the chemical at issue is transferred into the swelling cell. Propellants, or other volatile components can be transferred into the cell via suitable valving. Teflon tape may be used as necessary to ensure adequate seals. The quality of the seal should be confirmed by immersing the closed cell in a room temperature waterbath to look for gas bubbles or other indicia of a leak. In addition to looking for visually observable phenomena, measurements, e.g., pH, conductivity, or the like, can be made of the bath water in order to confirm the integrity of the seals. The inner and outer diameters are again measured after 1 day, 3 days, 7 days, 14 days, and 21 days to within 0.0005 inches (0.0013 cm). The percentage change in the inner and outer diameters is easily calculated according to the expression $$\% \text{ Swelling} = \frac{(\text{Final diameter} - \text{Initial Diameter})}{\text{Initial Diameter}} \times 100$$

Desirable elastomers also provide gaskets that have a percentage weight loss of less than 3%, preferably less than 1% when stored at 25° C. and 65% relative humidity for at least 7 days, preferably 14 days, more preferably 28 days. To test for leakage, the formulation at issue is placed into a specified number of vials, typically 2 to 20, each vial being fitted with one or more gaskets formed from the candidate gasket material(s). The initial weight of each vial is carefully recorded to the nearest 0.1 mg. The vials are then stored under the designated storage conditions. After the appropriate interval, e.g., seven days, fourteen days, and 28 days, the vials are weighed again. The vials may be returned to storage for one or more additional testing intervals. The percentage weight loss is given by the expression $$\% \text{ weight loss} = \left(\frac{Wi - Wn}{Wi}\right) \times 100\%$$

wherein Wi is the initial weight, in grams; and Wn is the weight as measured at the end of the designated interval, in grams.

With these criteria in mind, selecting a suitable elastomer or combination of elastomers that could be used in one or more of gaskets 42, 44, and 46 will depend to a large extent upon the type of ingredients incorporated into supply 18. One of ordinary skill in the art, with due consideration to these criteria, will be able to screen a number of elastomer samples in order to choose the most suitable elastomer material(s). Representative examples of elastomers that could be screened for incorporation into the gaskets 42, 44, and 46 include butyl rubber, ethylene-propylene-diene rubber (EPDM, commercially available under the trade designation KL70L038 from Kirkhill Rubber Co., Brea, Calif.), neoprene, butadiene-acrylonitrile copolymers ("buna"), copolymers of 80 to 95 weight percent of ethylene and 5 to 20 weight percent of an alkene (e.g., 1-butene, 1-hexene, 1-octene, or the like) such as the FLEXOMER DFDA 1085 and/or FLEXOMER DFDB 1085 copolymers available from Union Carbide, fluoropolymer rubber, polyurethane, polyamide (e.g., a nylon), rayon, polyolefin, combinations of these, and the like. Most preferably, ferrule gasket 42 comprises the DFDA 1085 and/or DFDB 1085 elastomers, and tank seal gasket 44 and diaphragm 46 each comprise the EPDM rubber.

Referring again to FIGS. 1 to 4a, actuator system 10 includes base section 54 having receptacle 56, as one main element, and a dispensing section 70, preferably in the form of a vented, funnel-shaped shroud, as another main element. Receptacle 56 is formed from sidewall 58 coupled to stem receiving section 59. These components define chamber 60 having bottom wall 62. A longitudinal axis of receptacle 56 extends from top end 64 to bottom wall 62. Receptacle 56 thus is open at its top end 64. This allows vial 14 to be inserted into receptacle 56 in order to carry out acutator operations. Receptacle 56 is adapted to receive vial 14 in a manner such that valved dispensing element 16 faces downward and is proximal to bottom wall 62. In the preferred embodiment shown, sidewall 58 is cylindrical to correspond to the shape of vial 14. Of course, sidewall 58 may have any convenient geometry so long as vial 14 can be positioned and supported in receptacle 56 during actuator operation. For example, if vial 14 were to have a rectilinear cross-section instead of a cylindrical cross-section, sidewall 58 preferably would have a corresponding rectilinear shape as well.

Figure 4A:
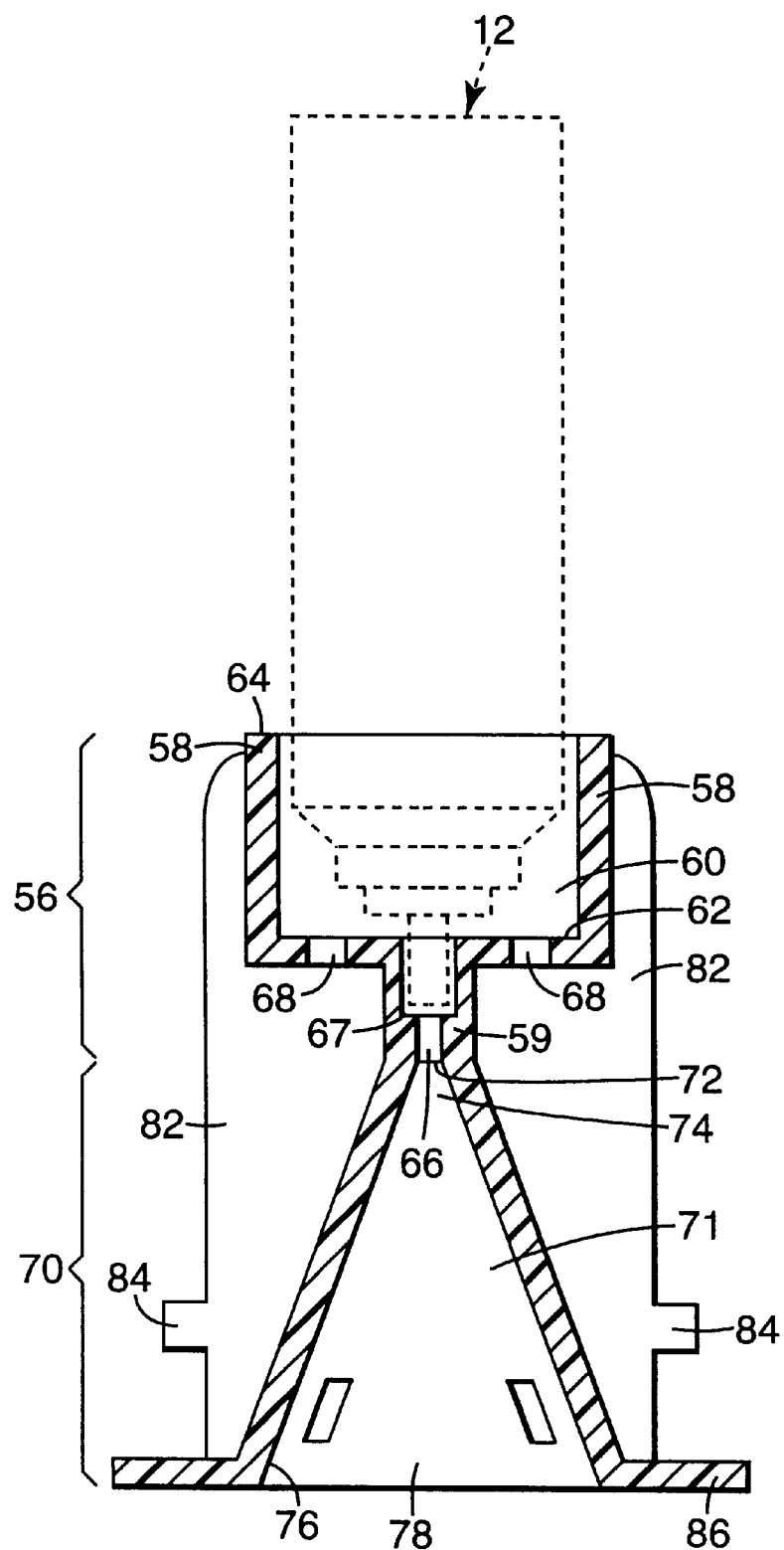
FIG. 4a is a cross-sectional side view of the base section used in the actuator system of FIG. 1.
Figure 4B:
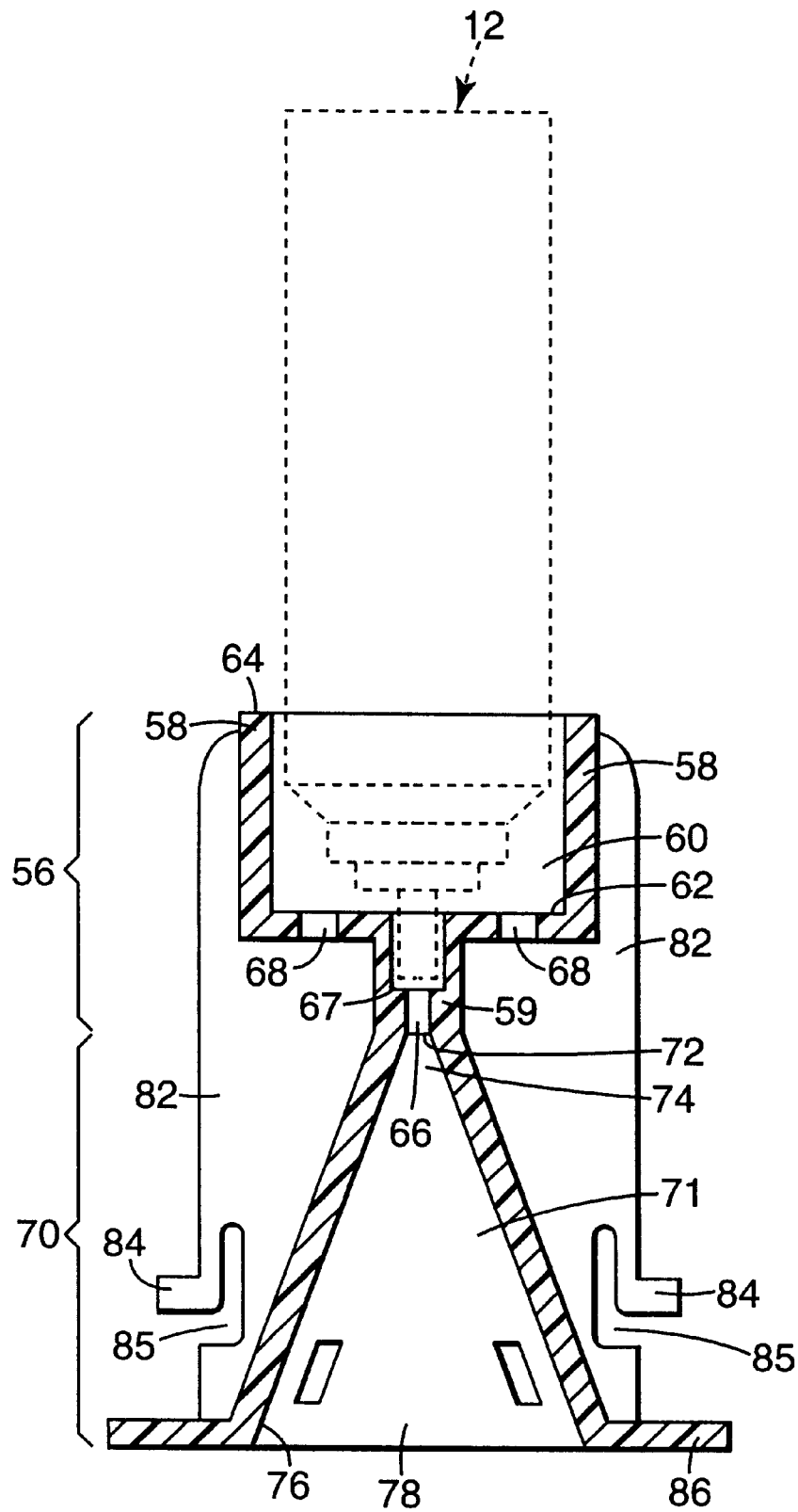
FIG. 4b is an alternative embodiment of a base section such as that shown in FIG. 4a except in FIG. 4b the ribs on the base section include cut-out portions proximal to the fingers to make it easier to resiliently depress the fingers when removing or placing a sleeve onto the base section.

Stem receiving section 59 includes centrally located orifice 66. Orifice 66 provides a passage through which a portion of supply 18 can be sprayed from vial 14 into interior 71 of dispensing section 70. With further reference to FIGS. 4a and 4b in addition to FIGS. 1 to 5, orifice 66 is generally configured such that stem 32 of valved dispensing element 16 is positioned within orifice 66 against orifice shoulder 67. Shoulder 67 and stem 32 cooperate to face 27 of element 16 far enough above bottom wall 62 so that stem 32 can be operationally depressed to open and close element 16 for dispensing the metered dose of formulation from metering chamber 26.

Still referring primarily to FIGS. 1 to 4a, receptacle 56 also preferably includes at least one vent to allow pressure in receptacle to be equalized with ambient pressure during actuator operation as will be described in more detail below.

In the preferred embodiment shown, such venting is provided by a plurality of vents 68 positioned circumferentially around orifice 66, although one or more vents (not shown) optionally could have been provided in sidewall 58 instead of or in addition to those provided in stem receiving section 59.

Base section 54 also includes dispensing section 70 extending from the bottom end of receptacle 56. The dispensing section 70 includes an interior 71 having throat 74 at top end 72 and mouth 78 at bottom end 76. Throat 74 is in open communication with orifice 66 allowing an amount of supply 18 to be sprayed on demand from vial 14 into interior 71 of dispensing section 70. The sprayed material leaves the dispensing section 70 through mouth 78 to be deposited onto host 11. Dispensing section 70 has a longitudinal axis extending from throat 74 to mouth 78. This longitudinal axis is substantially aligned with the longitudinal axis of receptacle 56 so that the sprayed formulation travels from vial 14 to the host 11 along a substantially linear path at least through dispensing section 70.

As shown, dispensing section 70 has a preferred funnel shape with a relatively narrow end corresponding to throat 74 and a relatively wide end corresponding to mouth 78. The funnel-shape of dispensing section 70, in combination with the linear path of material being sprayed through dispensing section 70, helps to promote uniform spray application each time the actuator is used. For example, actuator system 10 of the present invention can spray a consistent amount of material from a uniform height over a uniform area of host 11 to ensure consistent application onto host 11 time after time. This is particularly important for applications in which the "patch in a bottle" technology (identified above) is used to apply transdermal (or other transtissue), pharmacologically active patches onto host 11 for therapeutic treatment.

Preferably, dispensing section 70 also includes one or more vents 80 that help to dissipate propellant from interior 71 to the ambient in those embodiments in which supply 18 includes a propellant. Vent(s) 80 also help equalize pressure between dispensing section 70 and the ambient during actuator operations. Vents 68 advantageously allow volatile components of an aerosol spray to be vented to the ambient so that pressure build up inside of dispensing section 70 can be released without dislodging base section 54 from host 11 during actuation.

Base section 54 preferably further includes a plurality of longitudinal ribs 82 extending along the length of base section 54. Ribs 82 help to strengthen and provide structural support for receptacle 56 and dispensing section 70 so that base section 54 resists twisting or bending during actuator operations. Ribs 82 also provide guiding surfaces that slidably engage and support sleeve 88 (described further below) during actuator operation. As another preferred feature of base section 54, flange 86 extends radially outward from bottom end 76. Flange 86 provides a supporting surface that helps to stabilize actuator system 10 when placed onto host 11. Flange 86 also provides a means for attaching cover 100 (described further below) to dispensing section 70 over mouth 78 when actuator system 10 is not being used.

Sleeve 88 is in the form of a hollow cylinder formed from cylindrical sidewall 90 and top panel 92. The bottom end 94 of sleeve 88 is open, allowing sleeve 88 to fit over vial 14 and base section 54 as shown in FIG. 2. The user of actuator system 10, who might be host 11 or perhaps a medical professional assisting host 11, can move sleeve 88 up and down over base section 54 through a range of motion including a first, top position and a second, bottom position. In the first, top position, sleeve 88 is raised up far enough so that a sufficiently low, or substantially no actuating force acts against valved dispensing element 16. Valved dispensing element is thus closed. When moved downward to a bottom, second position, an actuating force is caused to act against valved dispensing element 16 so that element 16 is opened. An amount of supply 18 is sprayed from vial 14 as a result.

Such an actuating force may be established using any convenient mechanism that causes valved dispensing element 16 to open in the desired manner. In a preferred embodiment as shown in which valved dispensing element 16 is a spring actuated mechanism that opens when an actuating force acts against stem 32, the actuating force results when top panel 92 of sleeve 88 pushes stem 32 downward against shoulder 67. The resultant force causes valved dispensing element 16 to open and thereby allow an amount of supply 18 to be sprayed onto host 11. As another advantage, the valved dispensing element 16, which includes spring 40, tends to push sleeve 88 upward, biasing sleeve 88 toward the first position. Of course, if valved dispensing element 16 did not have this biasing feature, sleeve 88 could be biased upward using any other conventional biasing means.

It is desirable to limit the range of motion of sleeve 88 to facilitate ease of operation and to avoid damaging vial 14. For example, if the user were able to push sleeve 88 too far downward in an effort to spray material onto host 11, valved dispensing element 16 could be crushed or otherwise rendered nonfunctional. As another possibility, canister body 14 could break, especially when canister body 14 is made from glass. Additionally, the user could force stem 32 too far down into orifice 66 in bottom 62 of receptacle 56. On the other hand, if movement of sleeve 88 upward were not limited, the user could inadvertently drop vial 14 and base section 54 by grabbing only sleeve 88 when attempting to carry actuator system 10. Accordingly, it is desirable to provide actuator system 10 with features to limit the range of motion of sleeve 88 between a desired highest position beyond which sleeve 88 cannot be raised and a desired lowest position below which sleeve 88 cannot be pushed. However, the mechanism preferably should still allow sleeve 88 to be completely removed when desired so that vial 14 can be placed into and removed from receptacle 56 as desired. Preferably, these range limiting features comprise cooperating means positioned on base section 54 and sleeve 88, respectively.

A preferred structure for limiting the range of motion of sleeve 88 between desired maximum first and second positions includes one or more finger-like projections extending from one of base section 54 and sleeve 88 and a cooperating slot on the other. For example, as shown best in FIGS. 1 and 4*a*, sleeve 88 includes one or more, preferably 2 to 4, slots 96 that receive cooperating fingers 84 extending from ribs 82 of receptacle 56. When sleeve 88 is fitted over vial 14 and base section 54, fingers 84 fit into slots 96. Each finger 84 is smaller in the longitudinal axial dimension than its slot 96. This allows sleeve 88 to be raised until fingers 84 reach the bottom of the slots 96. The range of motion of sleeve 88 on the downward direction is limited by the amount by which vial 12 can be pushed downward when stem 32 is depressed. In order to provide a larger surface area for fingers 84 to bear against at the top and bottom of slots 96, slots 96 preferably are positioned in longitudinal ribs 98 positioned along at least a portion of the length of sleeve 88. Ribs 98 also help to reinforce sleeve 88 so that sleeve 88 has less of a tendency to be compressed, twisted, or otherwise distorted when pushed downward to actuate valved dispensing element 16.

Ribs 98 also provide a convenient means for gripping sleeve 88. From the inside of sleeve 88, the ribs 98 provide grooves 97 to slideably receive ribs 82 of base section 54 to help guide a sleeve 88 in its vertical travel. As seen but in FIG. 3b, the inside of sleeve 88 also may include additional ribs 95 to help maintain axial alignment of vial 12 relative to base section 84.

To make it easy to remove sleeve 88 from base section 54 when desired, sleeve 88 and/or base section 54 desirably include features allowing fingers 84 to be moved out of slots 96. This can be accomplished if fingers 84 are depressable or otherwise movable away from slots 96 in some fashion relative to sleeve 88. One skilled in the art could use any convenient approach to accomplish this. However, it is preferred that at least one of dispensing section 70 and/or sleeve 88 is resiliently deformable so that sleeve 88 can be removed from base section 54 merely by squeezing base section 54 to cause fingers 84 to deflect inward away from slots 96. FIG. 4b shows an alternative embodiment of a base section 54 identical to base section 54 of FIG. 4a except that ribs 82 of FIG. 4b include cutouts 85 proximal to each finger 84. Cutouts 85 allow fingers 84 to be resiliently depressed by a user to make it easier to place and remove sleeve 88 from base section 54. Sleeve 88 may also include optimal viewing slot 95 so that the contents of vial 12 can be visually observed, if desired.

When actuator system 10 is not being used to spray a desired material onto host 11, it is desirable to cover mouth 78 of dispensing section 70 to help maintain the cleanliness of interior 71 between actuator uses. It is also desirable to secure sleeve 88 in some fashion that prevents accidental spraying of supply 18. Cover 100 meets both of these objectives. Cover 100 includes bottom panel 102 that fits over mouth 78 of dispensing section 70 to keep dust, dirt, and other debris from collecting inside dispensing section 70 when actuator system 10 is not in use. Cover 100 includes arcuate sleeve 104 formed from sidewall 106 and arcuate top piece 108 that together define hollow 110. Arcuate sleeve 104 fits over flange 86 to help hold cover 100 in place over mouth 78. Preferably, the tolerances between arcuate sleeve 104 and flange 86 provide a friction fit, snap fit engagement, or the like, to help hold cover 100 in place. Tab 112 provides a convenient surface for gripping cover 100 when placing cover 100 over, or removing cover 100 from, base section 54. Cover 100 also includes an upward extending element in the form of ridge 114 that supports and helps hold sleeve 88 in the first position to physically prevent sleeve 88 from being accidentally depressed by the user.

Actuator system 10 is extremely easy to use for spraying medical formulations onto host 11. At the outset, sleeve 88 is removed from base section 54 allowing vial 14 to be placed into receptacle 56 with valved dispensing element facing downward toward bottom 62. Preferably, cover 100 is in place over mouth 78 during this phase of operations. Once vial 14 is in place, sleeve 88 can be fitted over vial 14 and base section 54, making sure that fingers 84 are properly seated in slots 96. With ridge 114 supporting sleeve 88 in the first position, fingers 84 are located proximal to the bottoms of slots 96. Actuator system 10 is now ready to be used. Cover 100 is removed, preferably just prior to spraying, and actuator system 10 is then placed over the desired surface of host 11 with flange 86 seated against that surface. Now, the user can pull or push, as the case may be, sleeve 88 downward. This actuates valved dispensing element 16, causing an amount of supply 18 to be sprayed through interior 71 onto host 11. After spraying, actuator system 10 can be lifted off of host 11. Cover 100 may then be replaced over mouth 78, and actuator system 10 is ready to be stored until the next desired use.

Figure 6:
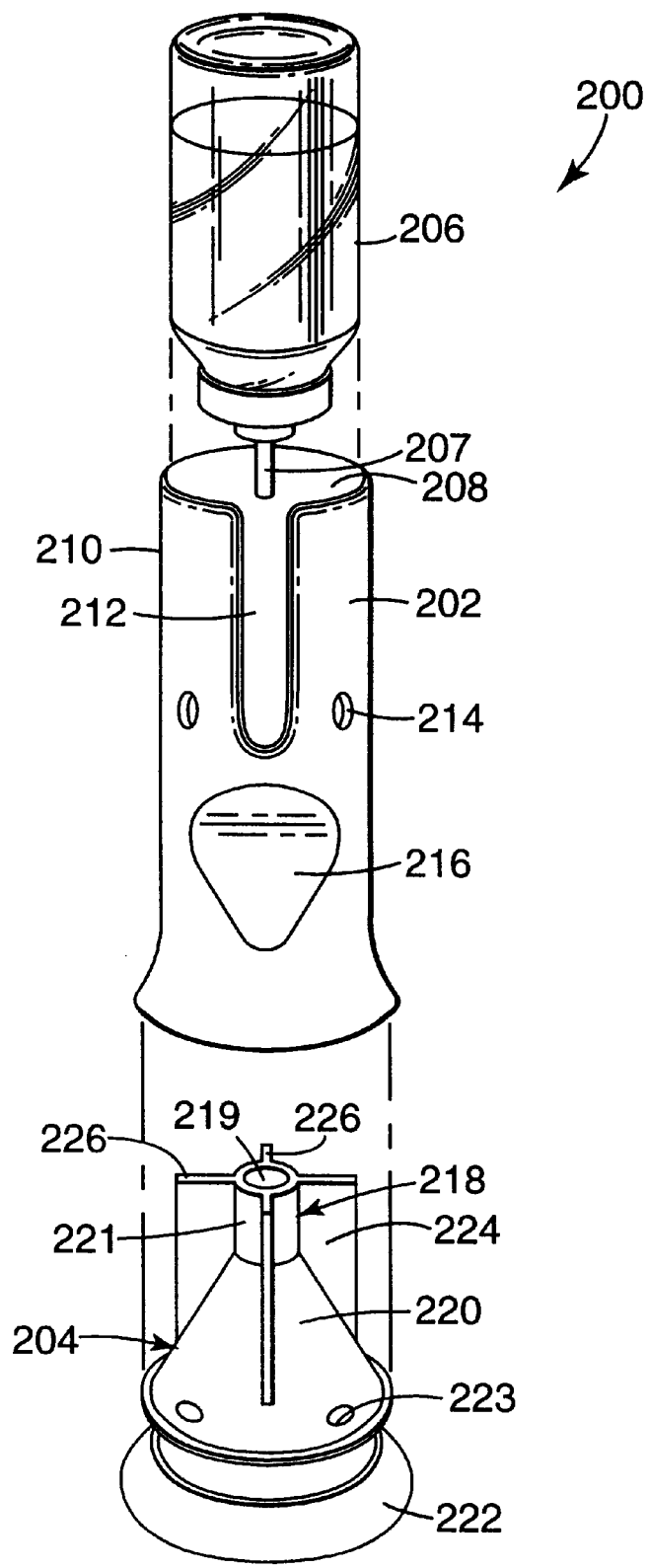
FIG. 6 is a perspective view of an alternative embodiment of an actuator system of the present invention.

An alternative embodiment of the present invention in the form of actuator system 200 is shown in FIG. 6. There, actuator system includes sleeve 202 and base section 204. Vial 206 fits inside chamber 208 of sleeve 202. Sidewall 210 of sleeve 202 has slot 212 to allow the contents of vial 206 to be visually monitored. Vents 214 are also provided to avoid pressure build up inside chamber 208 during use. Finger grips 216 provide a convenient comfortable means for holding sleeve 202 .

Base section 204 includes receptacle 218 and funnel-shaped dispensing section 220. Receptacle 218 comprises stem receiving section 221 having orifice 219 configured to receive valve stem 207 of vial 206. Dispensing section 220 is coupled to the bottom of receptacle 218 and provides constraining boundaries so that the sprayed formulation is dispensed onto a precisely defined area of the host from a precise height above the host. Dispensing section 220 includes vents 223 to permit gaseous components of the sprayed formulation, e.g., a propellant, solvent, or the like, to escape to the ambient. Rubber gasket 222 engages the bottom end of funnel section 220 and helps to form an effective seal between funnel section 220 and the surface onto which formulation is being sprayed.

Sleeve 202 in this embodiment is open at both the top and bottom ends. Thus, to help support vial 206 during use, ribs 224 extended outward from dispensing section 204 and provide a plurality of planar support surfaces 226 upon which vial 206 can be supported when valve stem 207 is depressed. In the sense that a purpose of receptacle 218 is to support and couple vial 206 to base section 204, planar support surfaces 226 can be considered to be part of receptacle 218. Ribs 224 also help to strengthen dispensing section 204 as well.

In use, stem 207 is fitted into orifice 219 while sleeve 202 is fitted around vial 206. The user places gasket 222 firmly against the desired substrate surface, holding system 200 in place with one hand. The palm or thumb of the other hand is placed over the bottom of vial 206, with the fingers engaging the flared portion of sleeve 202 at finger grips 216. The user gently pushes downward on vial 206 and sleeve 202 in order to depress valve and dispense a metered amount of formulation from a precise height onto a precise area of the substrate.

Figure 7:
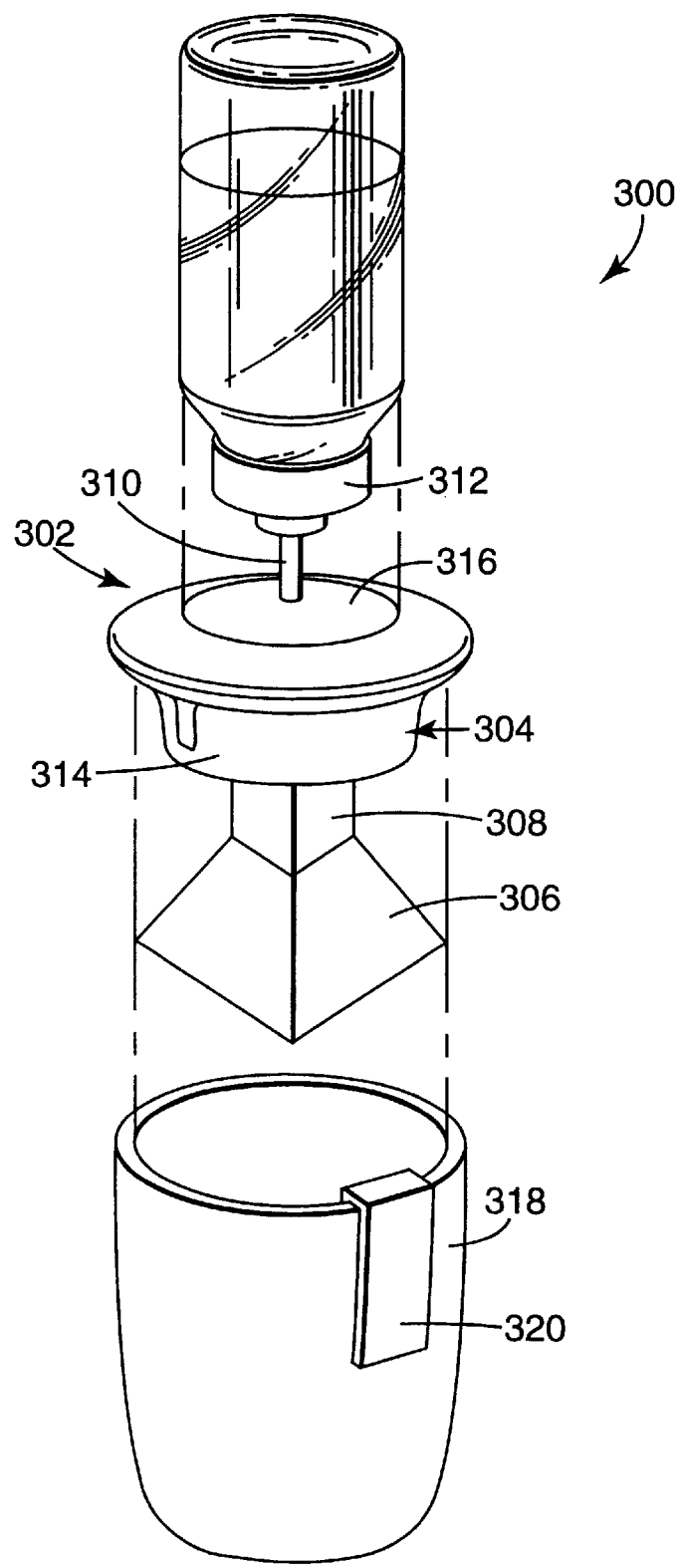
FIG. 7 is a perspective view of another alternative embodiment of an actuator system of the present invention.

An alternative embodiment of the present invention in the form of actuator system 300 is shown in FIG. 7. System 300 includes base section 302 including receptacle 304 and funnel-shaped dispensing section 306. Receptacle 304 includes stem receiving section 308 including an orifice (not shown) to receive stem 310 of vial 312. Cylindrical section 314 of receptacle 304 defines pocket 316 in order to help support vial 312. Cover 318 fits over funnel-shaped dispensing section 306 when system 300 is not being used to dispense a formulation onto a host. Cover 318 includes tab 320 that engages rim of cylindrical section 314 to make is easier to remove or replace cover 318.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. An actuator system for applying a sprayable formulation from a vial onto a limited surface area of a host, comprising:

(a) a base section comprising:
  (i) a dispensing section having an interior through which an amount of the formulation can be sprayed onto said surface area, wherein the dispensing section comprises a throat at which the amount of the formulation enters the dispensing section and a mouth at which the amount of the formulation exits the dispensing section, and wherein the dispensing section comprises at least one vent in open communication with the ambient; and
  (ii) a receptacle comprising a structure that operationally couples the vial to the dispensing section so that the formulation can be dispensed from the vial into the throat of the dispensing section; and
(b) a sleeve adapted to fit over at least a portion of the vial when the vial is positioned in the receptacle, wherein the sleeve has a range of motion extending from a first position to a second position, wherein movement of the sleeve from the first position to the second position causes said amount of formulation to be dispensed into the dispensing section, wherein the vial is closed when the sleeve is in the first position, and wherein the sleeve is biased toward the first position.

2. The actuator system of claim 1, wherein the dispensing section has a substantially linear longitudinal axis extending from the throat to the mouth of the dispensing section; and wherein the receptacle structure couples the vial to the dispensing section in a manner such that the amount of formulation is discharged into the dispensing section along a linear pathway that is substantially aligned with the longitudinal axis of the dispensing section.

3. The actuator system of claim 1, wherein the movement of the sleeve between the first and second positions is a linear motion guided by cooperating structures on the sleeve and the base section.

4. The actuator system of claim 3, wherein the cooperating stuctures comprise a plurality of longitudinal grooves extending along at least a portion of the length of one of the sleeve and the base section and a corresponding plurality of longitudinal ribs that slideably engage the grooves on the other of said base section and sleeve.

5. The actuator system of claim 1, wherein the interior of the sleeve comprises at least one projecting member that helps to maintain the vial in alignment with the base section when the sleeve is fitted over the vial.

6. The actuator system of claim 5, wherein said projecting member comprises a plurality of longitudinal, interior ribs extending along at least a portion of the length of the sleeve interior.

7. The actuator system of claim 1, further comprising a cover that releasably fits over the mouth of the dispensing section, said cover including an upward extending element that helps to constrain the sleeve in the first position.

8. The actuator system of claim 1, wherein the sleeve and base section comprise cooperating means for limiting the range of sleeve motion between the first and second positions.

9. The actuator system of claim 1, wherein at least one of the sleeve and base section comprises at least one extending projection and the other comprises a slot, wherein the extending projection and the slot cooperate with each other to limit the range of sleeve motion between the first and second positions.

10. The actuator system of claim 1, wherein the dispensing section comprises a funnel-shape with a relatively small end and a relatively wide end, said relatively small end corresponding to the throat of the dispensing section and said relatively wide end corresponding to the mouth of the dispensing section.

11. The actuator system of claim 1, wherein the receptacle comprises at least one vent allowing pressure build up to be released from the receptacle as the sleeve is moved between the first and second positions.

12. The actuator system of claim 11, wherein said at least one vent is positioned in the receptacle in a manner effective to provide open communication between the receptacle and the ambient.

13. The actuator system of claim 1, wherein the base section comprises a plurality of longitudinal ribs that slideably engage and help support the sleeve as the sleeve is moved between the first and second positions.

14. An actuator system for applying a sprayable formulation from a vial onto a limited surface area of a host, comprising a base section that includes:
(a) a shroud through which an amount of the formulation can be sprayed onto said surface area, wherein the shroud comprises a throat at which the amount of the formulation enters the shroud and a mouth at which the amount of the formulation exits the shroud, wherein the shroud comprises at least one vent in open communication with the ambient; and
(b) a receptacle comprising a structure that operationally couples the vial to the shroud so that the formulation can be dispensed from the vial into the throat of the shroud.

15. An actuator system for applying a sprayable formulation from a vial onto a defined surface area of a host, said actuator system comprising a base section that includes:
(a) a dispensing section comprising a pathway through which an amount of the formulation may be sprayed from a uniform height over said surface area, wherein the dispensing section comprises a substantially linear longitudinal axis extending from a throat at which the amount of formulation enters the dispensing section to a mouth at which the formulations exits from the dispensing section, and wherein the dispensing section comprises at least one vent in open communication with the ambient; and
(b) a receptacle comprising a structure that operationally couples the vial to the dispensing section so that the amount of the formulation can be dispensed from the vial through the dispensing section, wherein the receptacle comprises a cup for housing at least a portion of the vial, said cup comprising one or more vents providing open communication between the cup and the ambient.

16. An actuator system for applying a sprayable formulation from a vial onto a limited surface area of a host, comprising:
(a) a base section comprising:
  (i) a dispensing section having an interior through which an amount of the formulation can be sprayed onto said surface area, wherein the dispensing section comprises a throat at which the amount of the formulation enters the dispensing section and a mouth at which the amount of the formulation exits the dispensing section; and
  (ii) a receptacle comprising a structure that operationally couples the vial to the dispensing section so that the formulation can be dispensed from the vial into the throat of the dispensing section; and
(b) a sleeve adapted to fit over at least a portion of the vial when the vial is positioned in the receptacle, wherein the sleeve has a range of motion extending from a first position to a second position, wherein movement of the sleeve from the first position to the second position causes said amount of formulation to be dispensed into the dispensing section, wherein the vial is closed when the sleeve is in the first position, and wherein the sleeve is biased toward the first position, and wherein at least one of the sleeve and base section comprises at least one extending projection and the other comprises a slot, wherein the extending projection and the slot cooperate with each other to limit the range of sleeve motion between the first and second positions.

17. An actuator system for applying a sprayable formulation from a vial onto a limited surface area of a host, comprising:

(a) a base section comprising:
   (i) a dispensing section having an interior through which an amount of the formulation can be sprayed onto said surface area, wherein the dispensing section comprises a throat at which the amount of the formulation enters the dispensing section and a mouth at which the amount of the formulation exits the dispensing section; and
   (ii) a receptacle comprising a structure that operationally couples the vial to the dispensing section so that the formulation can be dispensed from the vial into the throat of the dispensing section; and (b) a sleeve adapted to fit over at least a portion of the vial when the vial is positioned in the receptacle, wherein the sleeve has a range of motion extending from a first position to a second position, wherein movement of the sleeve from the first position to the second position causes said amount of formulation to be dispensed into the dispensing section, wherein the vial is closed when the sleeve is in the first position, and wherein the sleeve is biased toward the first position, and wherein the base section comprises a plurality of longitudinal ribs that slideably engage and help support the sleeve as the sleeve is moved between the first and second positions.

* * * * *